United States Patent
Sheckler et al.

(10) Patent No.: US 6,702,784 B1
(45) Date of Patent: Mar. 9, 2004

(54) LIMITED INJECTION CYCLE SAFETY SYRINGE

(76) Inventors: Ross David Sheckler, 11402 North St., Cato, NY (US) 13033; Garvin Fitz Troy Forrester, 513 Village Blvd., South, Baldwinsville, NY (US) 13027

( * ) Notice: Subject to any disclaimer, the term of this patent is extended or adjusted under 35 U.S.C. 154(b) by 0 days.

(21) Appl. No.: 10/284,497

(22) Filed: Nov. 1, 2002

(51) Int. Cl.⁷ .................................................. A61M 5/00
(52) U.S. Cl. ....................... 604/181; 604/110; 604/111; 604/187; 604/198; 604/234
(58) Field of Search ................................. 604/110, 111, 604/181, 187, 192–9, 207–210, 220, 228, 234, 242

(56) References Cited

U.S. PATENT DOCUMENTS

| | | | |
|---|---|---|---|
| 4,801,295 A | 1/1989 | Spencer | 604/198 |
| 4,832,694 A | 5/1989 | Raphael, III et al. | 604/110 |
| 4,894,055 A | 1/1990 | Sudnak | 604/198 |
| 5,242,401 A | 9/1993 | Colsky | 604/110 |
| 5,411,487 A | 5/1995 | Castagna | 604/198 |
| 5,415,645 A | 5/1995 | Friend et al. | 604/110 |
| 5,433,712 A | 7/1995 | Stiles et al. | 604/197 |
| 5,984,899 A | 11/1999 | D'Alessio et al. | 604/198 |

*Primary Examiner*—Brian L. Casler
*Assistant Examiner*—Kathryn L. Thompson
(74) *Attorney, Agent, or Firm*—Bernhard P. Molldrem, Jr.

(57) ABSTRACT

A safety syringe employs a mechanical logic arrangement to control the movement of a spring-biased protective shield that covers the needle except during an injection, and which limits the number of injection cycles. The mechanical logic arrangement can include a series of parallel gated tracks, and a track follower pin disposed on the slide portion of the protective shield. There are one-way gates and redirection gates, which can be formed as flaps with a radial hinge in respect to the barrel axis. An alternative arrangement can employ a rotary cam. The number of injection cycles can be two or more, and the penetration depth for a given injection cycle can be controlled.

9 Claims, 4 Drawing Sheets

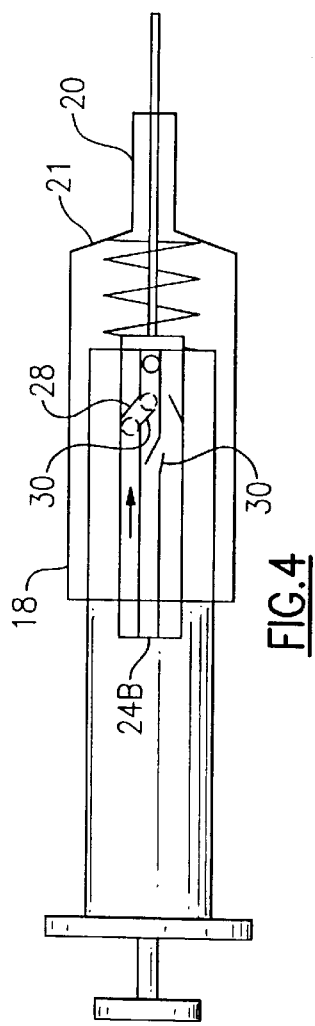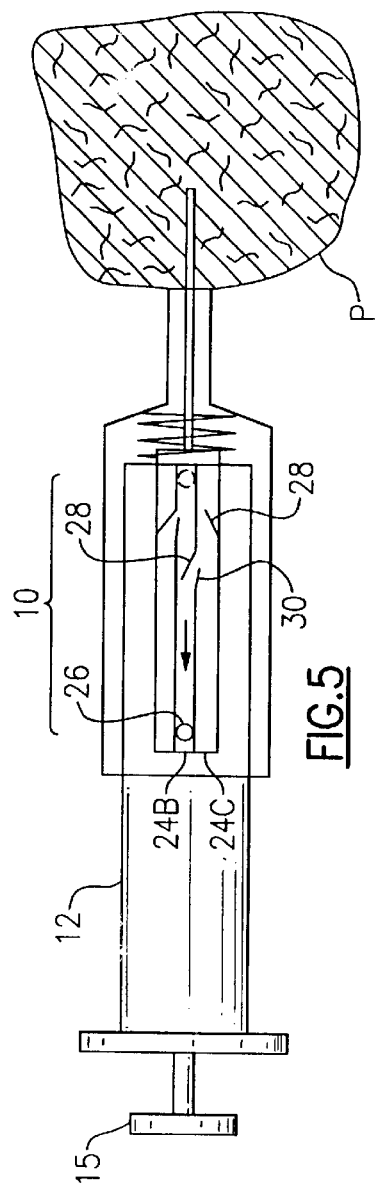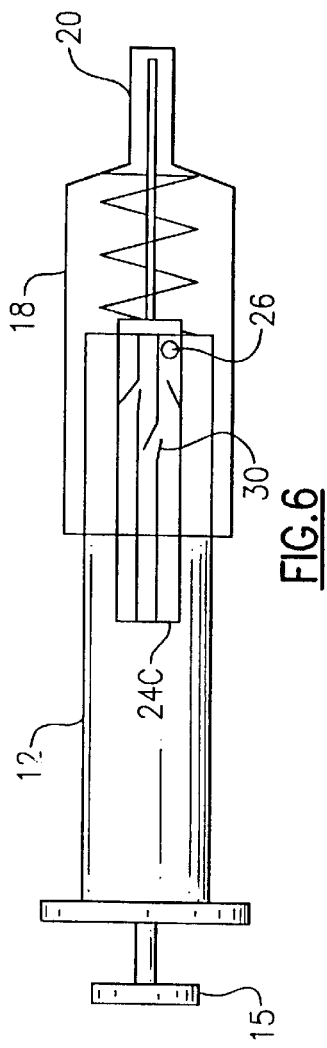

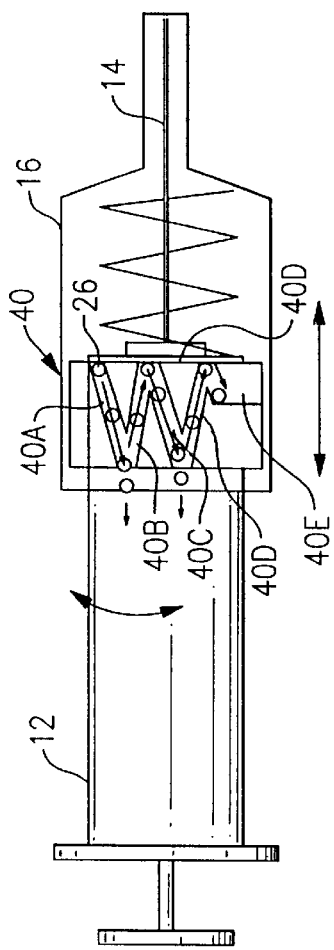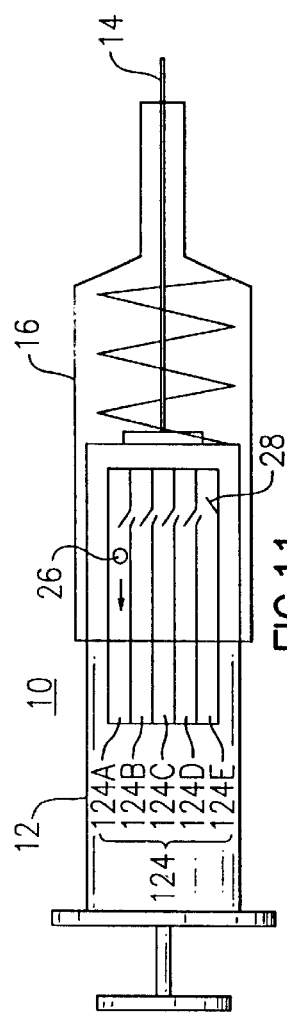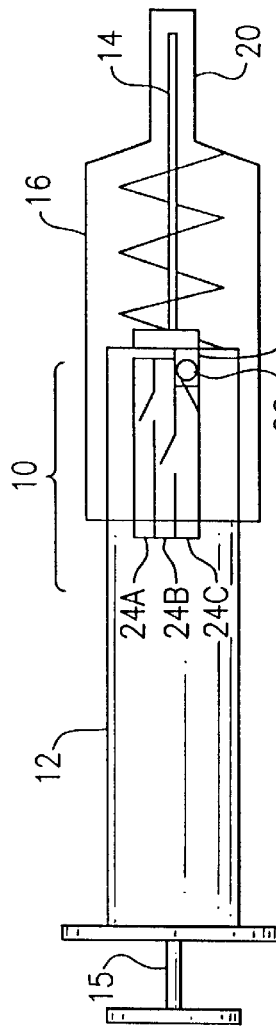

LIMITED INJECTION CYCLE SAFETY SYRINGE

BACKGROUND OF THE INVENTION

This invention relates to medical and surgical devices, namely syringes and hypodermic needles in which a medication is injected into a patient or by means of which blood or another fluid is withdrawn from a patient, and is more particularly concerned with a safety syringe in which the needle is shielded to protect patients and medical practitioners against accidental needle-stick injuries. The safety syringe is intended to protect the user from accidental puncture from the needle by means of a needle guard that shields the needle at all times other than during an injection procedure.

It is well appreciated that hypodermic needles present a danger of cross contamination, that is, spreading of pathogens that may be in a patient's body fluids, to other persons who may have to handle a syringe. Accidental sticking of the needle into a doctor or nurse is a common risk, and steps have been taken to reduce this risk by covering or shielding the needle between injection cycles and after injection cycles. The prior proposals have been far from foolproof, and many of these leave the needle exposed between injections, or may require the practitioner to use both hands to use the syringe, which makes the shield or cover inconvenient to use.

There remains a need for a safety syringe that avoids manual operation, that is, for a syringe in which the practitioner does not need to take any additional steps during an injection cycle, and in which the shield will remain over the needle except when the needle is inserted into a vial for filling the syringe and when the needle is actually being inserted into the patient to inject the medication. By the same token, there remains a need for an effective safety syringe that permits normal, one-hand operation without compromise of safety.

The safety syringe should also permit some limited number of injection cycles, in excess of a single cycle, so that it is possible to fill the syringe from a vial, and then inject the medication into the patient at one, two, or some other number locations. For example, it is sometimes necessary to apply a medicament or local anaesthetic to a patient on both sides of a wound, and the syringe should permit this. It is then desirable for the syringe to lock, with the shield covering the sharp needle, after the last of the injection cycles.

OBJECTS AND SUMMARY OF THE INVENTION

Accordingly, it is an object of the present invention to provide a safety syringe in which the needle is covered before, between, and after the injection cycles, and which avoids the drawbacks of the prior art.

It is another object to provide a safety syringe that is of a straightforward, simple design, and which does not require any special actions on the part of the practitioner.

It is a more specific object to provide a safety syringe with a spring-loaded shield that remains in the cover or guard position except during an injection cycle, which permits one-hand operation, and which locks in the cover or guard position after a predetermined Nth injection cycle.

It is another object to provide a safety syringe with the features of automatic limited cycle, one-hand operation, continuously guarded needle, and programmability (e.g., by manufacturer) for specific operation.

In accordance with one aspect of the present invention, a safety syringe is made with a a tubular barrel that has a proximal end and a distal end; a hollow needle affixed to the distal end of the barrel and extending distally from the barrel; and a protective shield that covers the needle and is movable proximally-distally so that the shield has a distal or extended protective position and a proximal exposed position. The protective shield has a tubular slide member that fits slidably over the distal end of the barrel and a needle cover that projects distally from the slide member out to cover the needle. A spring or other biasing device urges the slide member distally so that the protective shield goes its distally extended protective position. In that position, the needle cover extends distally beyond a tip of said needle so that the patient and practitioner are protected from the sharp end of the needle.

A series of gated tracks are provided on the barrel and a track follower that rides in the gated tracks is situated on a facing surface of the slide member. The track follower, which can be a radially oriented pin, projects into one of the tracks so it can follow the tracks, and pass through gates successively along the series of tracks. Alternatively, the tracks can be formed on the slide of said protective shield, with the pin or follower on the barrel of the syringe.

The gated tracks are arranged such that the protective shield is initially disposed in its protective position. The follower travels in the tracks, back and forth, in sequence to permit the shield to retract proximally to the exposed position, and then back to the covered or protective position. The follower travels from one track to another in turn to permit the shield to extend to the protective position after a first injection cycle; then in a successive one of the tracks to permit the shield to retract to the exposed position for at least one further injection cycle; and then the follower travels to reach a lock position at a final injection cycle.

In some of many possible preferred embodiments the series of tracks includes three tracks, and said track follower reaches a lock position in the third tracks at the end of a second injection cycle. Alternatively, there can be at least four tracks, so that the track follower reaches the lock position at the end of a predetermined injection cycle beyond a second injection cycle, i.e., after three or after four injection cycles. In other alternative embodiments, one track in the series of tracks provides a selective lock position in which the shield is held in a proximal position in which the needle is at least partly exposed.

The tracks or channels can be of programmed lengths to accommodate the need to limit the depth of injection. With a given track shortened or lengthened the needle can be limited to a shallower injection depth or permitted to go to a deeper injection depth, as required for a given application.

Favorably, the gates included in the gated tracks are in the form of uni-directional flaps with a hinge axis that is directed radially, in respect to the barrel of the syringe.

An alternative embodiment the series of gated tracks or channels can be on a sleeve that rotates around the circumference of the barrel of the syringe, controlling the shield extension and retraction with cam action.

An important aspect of this invention lies in the use of one-way gates, redirection gates, and programmed channel lengths to create a logical sequence to control the action of the shield. The arrangement of the tracks or channels can be manifested in many forms.

The safety needle of this invention is fully automatic, with the shield sliding out of the way upon injection and sliding back over the needle when the injection is complete. The safety syringe arrangement of this invention automatically limits the number of injections for which the syringe can be used, thus preventing a needle that has been used on one patient from contacting a practitioner or another patient. The incorporation of mechanical logic allows the practitioner to operate the syringe with one hand, except when the logic sequence requires a manual input, such as to unlock from a lock position.

The automatic, limited cycle operation is achieved through a variety of mechanical logic mechanism that are built into the syringe at the time of manufacture. A basic-cycle logic sequence, or standard sequence, would be inject vial—inject patient—lock. However, the syringes can be produced with other logic sequences by altering the mechanical logic at the time of manufacture. One alternative logic sequence could be inject vial—inject patient—hold open—manual release—lock.

The above and many other objects, features, and advantages of this invention will be more fully appreciated from the ensuing description of a few selected preferred embodiments, which is to be read in conjunction with the accompanying Drawing.

BRIEF DESCRIPTION OF THE DRAWING

FIGS. 2 to 6 are schematic views of the safety syringe of this embodiment showing in sequence the safety syringe being injected into a vial, drawing material from the vial, between cycles, injecting the material into a patient, and post injection.

FIG. 10 shows another embodiment which employs a rotary cam.

FIG. 11 shows an alternative embodiment in which there can be a larger number of injection cycles.

FIG. 12 shows a further alternative arrangement in which the guard is further extended over the needle following a final injection cycle.

DETAILED DESCRIPTION OF THE PREFERRED EMBODIMENT

Figure 1:
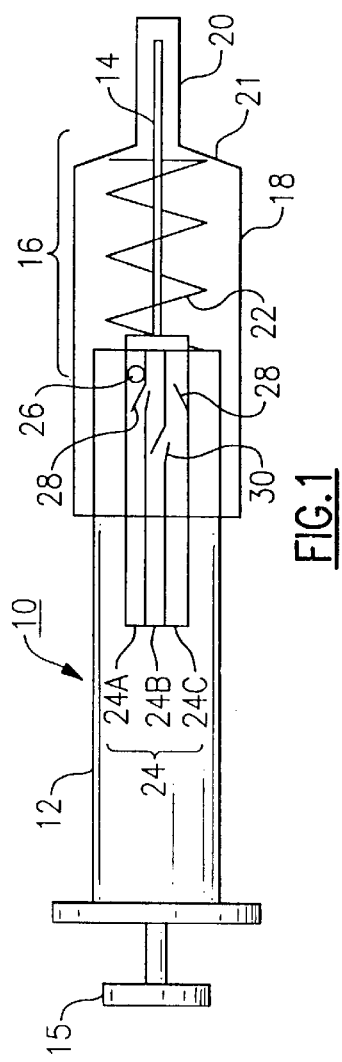
FIG. 1 is a schematic view of a safety syringe according to an embodiment of the present invention.

With reference now to the Drawing, FIG. 1 shows a safety syringe 10 according to an embodiment of this invention. The syringe 10 has a generally cylindrical barrel 12, with a hollow needle 14 extending from its distal end. A plunger or piston 15 is positioned within the barrel 12 and extends out from its proximal end. In this embodiment a protective needle guard or shield 16 is positioned over the distal portion of the barrel 12 and needle 14, and includes a generally cylindrical slide portion 18 that fits over the barrel and a needle cover portion 20 that is of narrower diameter than the slide portion 18 and fits over the needle 14. The distal end of the needle cover 20 is open to permit the needle to be exposed during an injection cycle, and there is a generally conic wall 21 joining the slide portion 18 and needle cover portion 20. A coil spring 22 is situated inside the slide portion 18 between the distal end of the barrel 12 and the wall 21 to urge the protective needle guard 16 distally, so that the needle cover portion 20 normally extends beyond the end of the needle 14.

A mechanical logic arrangement controls the number and depths of the injection cycles, and in this embodiment the mechanical logic comprises an arrangement 24 of parallel gated tracks 24A, 24B and 24C disposed on the barrel 12 of the syringe 10, and oriented parallel to the axis of the syringe. The tracks 24A, 24B, 24C are in the form of channels, and these guide the travel of a follower 26, which here is in the form of a pin that projects radially inwardly from the inside surface of the slide member 18. The pin or follower is guided from each gated track 24A, 24B to the next 24B, 24C by means of one-way gates 28 and redirection gates 30. These gates can be in the form of flaps that are arranged radially and that are hinged in a radial manner with respect to the axis of the syringe 10.

Figure 2:
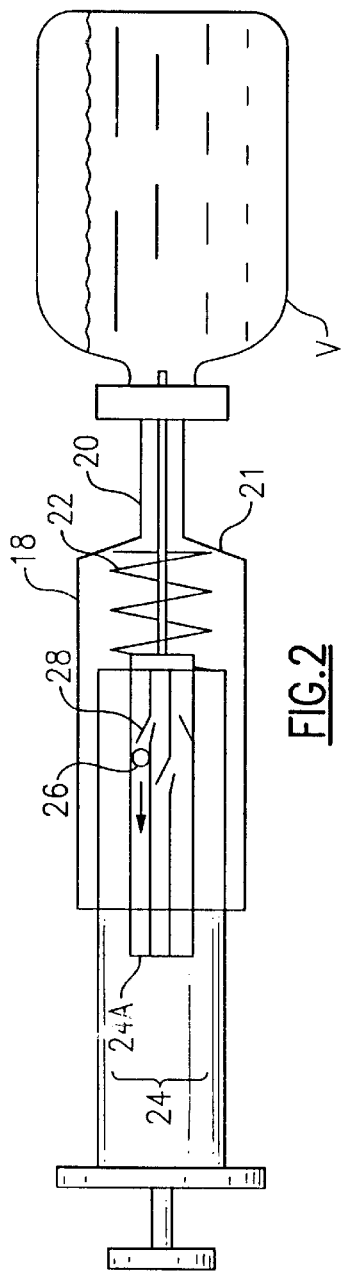
Figure 3:
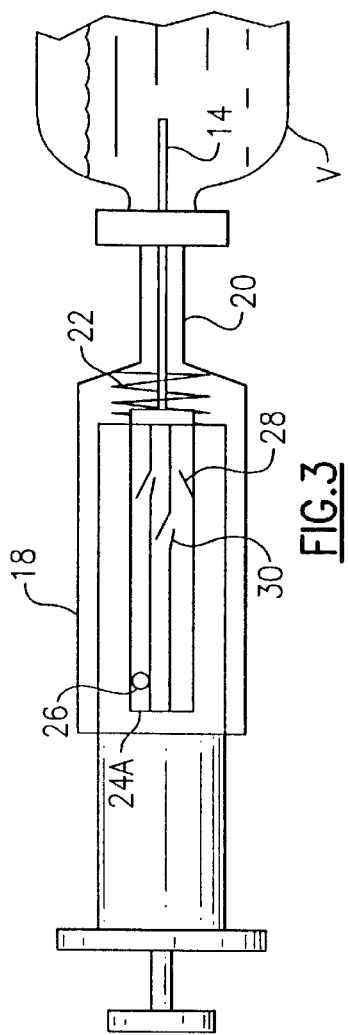

Initially, as shown in FIG. 1, the syringe 10, as it comes from the supplier, has the protective shield 16 biased distally outward with the pin follower 26 situated at the distal end of the first track 24A. Then, in order to fill the syringe 10, the practitioner pushes the needle end of the syringe onto the diaphragm of a vial V, as shown in FIG. 2, and this pushes the needle cover 20 and slide 18 back, i.e., proximally, so that the pin 26 travels past a one-way gate 28 and then out along the track 24A, as shown in FIG. 3. This compresses the spring 22. Now the practitioner can fill the syringe by drawing back the plunger 15 (this action is not shown). When the syringe 10 is withdrawn from the vial, the spring 22 urges the protective shield forward, i.e., distally, as shown in FIG. 4, so that the cover 20 protrudes past the end of the needle 14. During this motion, the follower pin 26 travels to the one-way gate 28, and a redirection gate 30 directs the pin 26 into the adjacent channel 24B.

The needle cover 20 remains in a protective position over the needle 14 until the syringe is used to inject the medication into a patient P. As shown in FIG. 5, pushing the needle 14 through the skin of the patient P deflects the needle cover 20 proximally, and the follower pin 26 travels proximally along the track 24B past a one-way gate 28 in that track. After the practitioner has injected the medication into the patient P, he or she withdraws the syringe, and the spring 22 pushes the protective shield forward, so that the needle cover 20 again projects beyond the end of the needle 14, as shown in FIG. 6. During this movement, the pin follower 26 travels back along the track 24B, and through another redirection gate 30 into the next track 24C. In this case, where the safety syringe is limited to two injection cycles, the third track 24C has a one-way gate 28 that is oriented to prevent the pin 26 from travel, so that the protective shield 16 remains held in the protective position and cannot be deflected to expose the needle 14.

Of course, the redirection gates, one-way gates, and the lengths of the channels or tracks can be arranged for a different mechanical programming, that is, to achieve a different number of injection cycles, or to limit injection depth, for example. Also, it is possible for the gates to be configured with flaps hinged along a circumferential line, rather than along a radial line. The channels or slots that comprise the arrangement 24 of tracks can be formed directly on the barrel 12, or may alternatively be formed on a sleeve that fits onto an existing syringe barrel. Also, while this embodiment shows the pin 26 on the inside of the slide 18 and the tracks 24 on the barrel 12, a reverse arrangement could be employed, with the pin 26 positioned on the barrel 12 and with the tracks 24 formed on the inside surface of the slide 18. Also, there can be a pair of similar tracks 24 and a pair of pins 26 on opposite sides of the syringe for a balanced operation.

Figure 7:
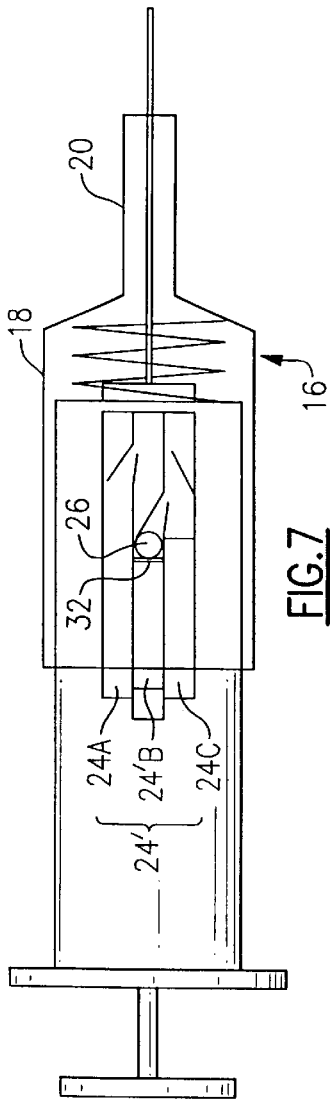
FIG. 7 shows another embodiment in which there is a limited depth injection cycle.

One alternative arrangement is illustrated in FIG. 7, in which the safety syringe employs an arrangement of tracks 24'. Here, the second track 24'B has a stop 32 that limits travel of the pin 26 in the proximal direction, and thus limits travel of the needle cover 20 to a programmed amount. This configuration can be employed where it is desired to limit the injection depth of the needle 14 into the patient P. The remaining elements of this safety syringe can be the same as with the first embodiment, and are identified by the same reference numbers, with no need to repeat their description. The stop 32 can be placed in any of the channels or tracks, depending upon the need for limiting the depth for any given injection cycle. It is also possible to lengthen any of the tracks or channels to permit more of the needle to be exposed for any given injection cycle.

Figure 8:
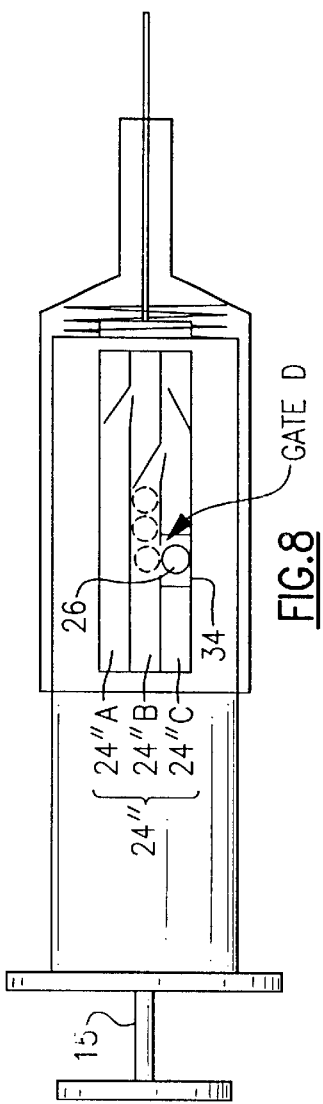
FIGS. 8 and 9 show alternate additional embodiments in which there is a locked open position in which the needle is selectively held exposed.

FIG. 8 illustrates another embodiment of the safety syringe of this invention in which its programmed track arrangement 24" has a lock position 34 formed in third track 24"C that can be accessed from the second track 24"B, e.g., by twisting the protective shield 16 relative to the syringe barrel 12. This embodiment can be used when it is desired to hold the needle cover 20 back to expose a portion of a needle 14. This permits the practitioner the option of multiple additional injection cycles, with the needle continuously exposed. When the last injection cycle is completed, the practitioner can simply twist the shield so that the pin 26 can travel back along the track 24"B to the locked position at the distal end of the track 24"C.

Figure 9:
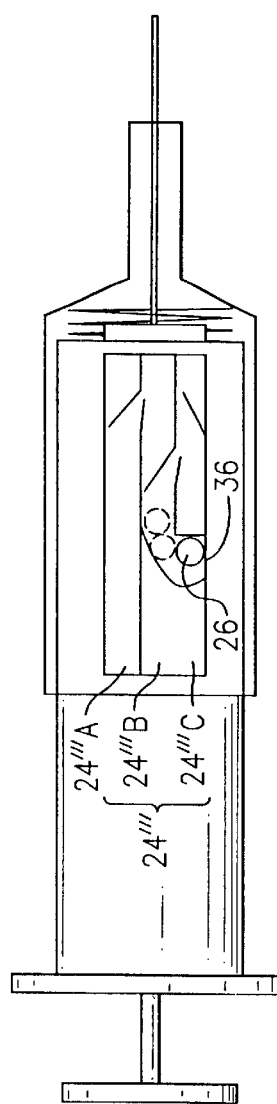

Another embodiment is shown in FIG. 9, in which the syringe can be set into a locked exposed position. Here, there is a set of tracks 24'" with a curved pathway 36 at a proximal part of the tracks 24'"B and 24'"C, so that the pin 26 travels to the lock position automatically. The syringe can be released from the locked position by twisting the shield 16 relative to the barrel 12, so that the pin 26 moves to the final position at the distal end of the track 24'"C.

As shown in FIG. 10, in some embodiments of this invention the syringe may employ a rotary cam or sleeve 40, in which there are a series of gated tracks or channels 40A, 40B, 40C, 40D. The cam 40 is fixed axially on the distal end of the barrel 12, but can rotate, as shown, when the slide portion 18 of the protective shield 16 moves back and forth. This permits the cam follower pin 26 to ride in the series of gated channels from an initial position at the distal end of the first channel 40A to a final locked position 40E at the distal end of the last channel 40D.

An embodiment that permits more than the two injection cycles of the foregoing embodiments is illustrated in FIG. 11, in which the elements that are the same as in the previous embodiments are identified with the same reference numbers. Here, the programmed mechanical logic includes a sequence 124 of parallel gated tracks 124A to 124E, such that there can be four injection cycles, with the pin 26 residing at the distal end of the final track 124E at the end of the last injection cycle, such that the needle cover 20 is situated over the needle 14 at the end of that injection cycle.

A further embodiment of this safety syringe 10 is shown in FIG. 12. Here, an extension 50 at the distal end of the final track 24C allows additional distal travel of the pin 26 and the protective shield 16. This leaves the needle cover 20 extending further past the distal, sharp end of the needle 14 in the locked position after the final injection cycle, for use when additional protection from needle-stick is desired.

While the invention has been described with reference to specific preferred embodiments, the invention is certainly not limited to those precise embodiments. Rather, many modifications and variations will become apparent to persons of skill in the art without departure from the scope and spirit of this invention, as defined in the appended claims.

We claim:

1. A safety syringe comprising
   a tubular barrel having a proximal end and a distal end;
   a hollow needle affixed to the distal end of said barrel and extending distally therefrom;
   a protective shield for covering said needle and movable proximally-distally between a distally extended protective position and a proximal exposed position; said protective shield including a tubular slide member that fits slidably over a distal end of said barrel and a needle cover projecting distally from said slide member over said needle, and spring means biasing said slide distally to urge the protective shield to its distally extended protective position in which the needle cover extends distally beyond a tip of said needle;
   a plurality of gated tracks situated on one of said barrel and the slide of said protective shield; and
   a track follower situated on a facing surface of the other of said barrel and said slide and projecting into one of said tracks to travel therealong and through gates thereof successively into others of said tracks;
   such that said protective shield is initially disposed in its protective position; with said follower traveling in said tracks to permit the shield to retract proximally to the exposed position; the follower traveling to another of said tracks to permit the shield to extend to the protective position after a first injection cycle; the follower traveling in a successive one of said tracks to permit the shield to retract to the exposed position for at least one further injection cycle, and said follower reaching a lock position at a final injection cycle.

2. The safety syringe of claim 1, wherein said plurality of tracks includes three tracks, and said track follower reaches a lock position in a third one of said tracks at the end of a second injection cycle.

3. The safety syringe of claim 1, wherein said plurality of tracks includes at least four tracks, so that the track follower reaches the lock position at the end of a predetermined injection cycle beyond a second injection cycle.

4. The safety syringe of claim 1, wherein plurality of tracks provides a selective lock position in which the shield is held in a proximal position in which the needle is at least partly exposed.

5. The safety syringe of claim 1, wherein said plurality of tracks are situated on a cam disposed on said barrel.

6. The safety syringe of claim 1, wherein said gated tracks include gates in the form of uni-directional flaps.

7. The safety syringe of claim 1, wherein follower includes a pin directed axially in respect to said barrel and engaging said tracks in turn.

8. The safety syringe of claim 1, wherein said gated tracks include a combination of unidirectional gates and redirection gates.

9. The safety syringe of claim 1, wherein said unidirectional gates permit travel in one direction therepast in a given one of said tracks, but block passage in the opposite direction, and wherein said redirection gates permit passage in one direction into a successive one of said tracks from said given one of said tracks.

* * * * *